United States Patent

Bowden et al.

Patent Number: 6,025,466
Date of Patent: Feb. 15, 2000

[54] CYCLIC HEPTA-PEPTIDE DERIVATIVE FROM COLONIAL ASCIDIANS, LISSOCLINUM SP.

[75] Inventors: Bruce Frederick Bowden, Townsville, Australia; Dolores Garcia Gravalos, Tres Cantos, Spain

[73] Assignee: Pharma Mar, s.a., Madrid, Spain

[21] Appl. No.: 09/171,332

[22] PCT Filed: Apr. 18, 1997

[86] PCT No.: PCT/GB97/01088

§ 371 Date: Feb. 19, 1999

§ 102(e) Date: Feb. 19, 1999

[87] PCT Pub. No.: WO97/39025

PCT Pub. Date: Oct. 23, 1997

[30] Foreign Application Priority Data

Apr. 18, 1996 [GB] United Kingdom .................. 9608010

[51] Int. Cl.[7] .............................. C07K 7/06; C07K 7/64
[52] U.S. Cl. .......................... 530/317; 530/329; 514/11; 514/16; 514/21
[58] Field of Search ................. 574/11, 16; 530/317, 530/329; 514/21

[56] References Cited

PUBLICATIONS

Isolation and Structure Determination of Didemnenones, Novel Cytotoxic Metabolites from Tunicates; J. Am. Chem. Soc. 1988, 110, 1308–1309; Niels Lindquist and William Fenical, David F. Sesin and Chris M. Ireland, Gregory D. Van Duyne, Craig J. Forsyth, and Jon Clardy; Jun. 26, 1987.
Novel Cytotoxic Compounds from the Ascidian *Lissoclinum bistratum*; Bernard M. Degnan, Clifford J. Hawkins, Martin F. Lavin, Elizabeth J. McCaffrey, David L. Parry, and Diane J. Watters; J. Med. Chem. 1989, 32, 1354–1359.
Varamines A and B, New Cytotoxic Thioalkaloids from *Lissoclinum vareau*; J. Org. Chem, vol. 54, No. 17, 1989; Mar. 3, 1989.
Varacin: A Novel Benzopentathiepin from *Lissoclinum vareau* That Is Cytotoxic toward a Human Colon Tumor; Bradley S. Davidson, Tadeusz F. Moninski, Louis R. Barrows, and Chris M. Ireland; J. Am. Chem. Soc. 1991, 113, 4709–4710.
Revised Structure of Bistramide A (Bistratene A): Application of a New Program for the Automated Analysis of 2D INADEQUATE Spectra; Mark P. Foster, Charles L. Mayne, Reinhard Dunkel, Ronald J. Pugmire, David M. Grant, Jean–Michel Kornprobst, Jean–Francois Verbist, Jean–Francois Biard, and Chris M. Ireland; J. Am. Chem. Soc. 1992, 114, 1110–1111.
Bistratamides C and D. Two New Oxazole–Containing Cyclic Hexapeptides Isolated from a Phillipine *Lissoclinum bistratum* Ascidian; Mark P. Foster, Gaseously P. Conception, Gina B. Canaan, and Chris M. Ireland; J. Or. Chem, 1992, 57, 6671–6675.

Proton Nuclear Magnetic Study of Bistramide A., a new cytotoxic drug isolated from *Lissoclinum Bistratum* Sluiter; D. Gouiffes, S. Moreau, N. Helbecque, J.L. Bernier, J.P. Henichart, Y. Barbin, D. Laurent, J.F. Verbist; Tetrahedron Vo. 44 No. 2, pp. 451 to 159, 1988.

Vycloxazoline: A Cytrotoxic Cyclic Hexapeptide from the Asicidian *Lissoclinum Bistratum*; Trevor W. hambley, Clifford J. Hawkins, Martin F. Lavin, Anna Van Den Break and Diane J. Waiters; Tetrahedron vol. 48, No. 2, pp. 341–348, 1992.

Nairaiamides A. and B. Two Novel Di–Proline Heptapeptides Isolated from a Figian *Lissoclinum bistratum* Ascidian Mar. P. Foster and Chris M. Ireland; Tetrahedron Letters, vol. 34, No. 18, pp. 2871–2874, 1993.

Marine Natural Products; D. J. Faulkner; Natural Product Reports, 1993, vol. 10, p. 497.

Carroll, et al., "Patellins 1–6 and Trunkamide A: Novel Cyclic Hexa–, Hepta and Octapeptides from Colnial Ascidians, Lissoclinum sp." Aust. J. Chem, 1996, 49, 659–667.

*Primary Examiner*—Michael P. Woodward
*Assistant Examiner*—A. Gupta
*Attorney, Agent, or Firm*—Ernest V. Linek; Banner & Witcoff, Ltd.

[57] ABSTRACT

A new cyclic heptapeptide, trunkamide A, with antitumor activity has been isolated from a Lissoclinium sp. collected on the Great Barrier Reef, Australia. The structure was determined to be of formula (I):

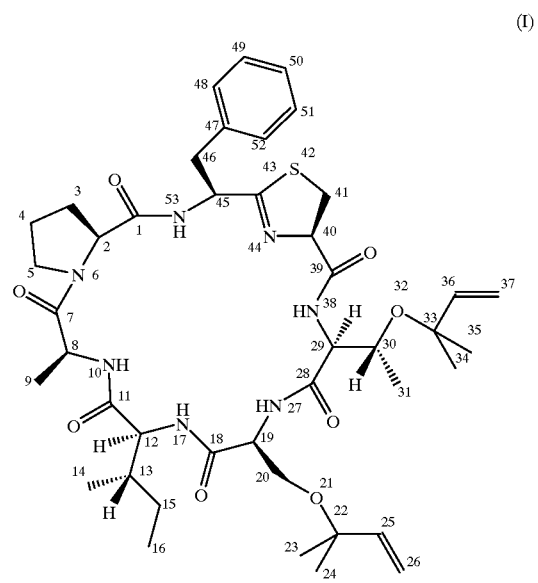

2 Claims, No Drawings

CYCLIC HEPTA-PEPTIDE DERIVATIVE FROM COLONIAL ASCIDIANS, LISSOCLINUM SP.

The present invention relates to trunkamide A.

BACKGROUND OF THE INVENTION

The genus Lissoclinum of ascidians has proven to be an extremely rich source of novel biologically active natural products. *Lissoclinum patella* for example has yielded over twenty thiazole-containing cyclic peptides, three highly cytotoxic thiazole-containing macrolides and an antibacterial polyketide lactone (Nat. Prod. Rep., 1994, 11, 355 and earlier reports in the series). Another species, *L. bistratum*, has been reported to produce cyclic hexapeptides (Tetrahedron, 1992, 48, 341; and J. Org. Chem.(1992, 57, 6671), heptapeptides (Tetrahedron Lett. 1993, 2871) and two extremely toxic spiro ketal amides (see J. Med. Chem., 1989, 32, 1354; Tetrahedron, 1988, 44, 451; and J. Am. Chem. Soc., 1992, 114, 11 10). *Lissoclinum (didemnum) voeltzkowi* produces antileukemic cyclopentenones (J. Amer. Chem. Soc., 1988, 110, 1308) while *L. vareau* produces bright red heteroaromatic pigments (J. Org. Chem., 1989, 54, 4256) and a benzopentathiepin which is cytotoxic to human colon tumors (J. Amer. Chem. Soc., 1991, 113, 4709).

SUMMARY OF THE INVENTION

The present invention provides the compound trunkamide A of formula:

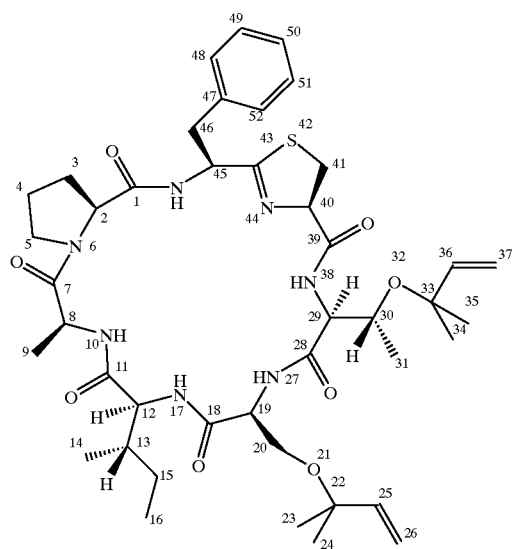

and pharmaceutically acceptable acid addition salts of Trunkamide A.

The compound of the present invention, Trunkamide A, exhibits antitumor activity against cell lines derived from human tumors. By way of illustration, the compound is active against the cell lines P-388 mouse lymphoma, A-549 human lung carcinoma, HT-29 human colon carcinoma and MEL-28 human melanoma. Accordingly, the present invention further provides a method of treating any mammal affected by a malignant tumor sensitive to Trunkamide A, which comprises administering to the affected individual a therapeutically effective amount of Trunkamide A or a pharmaceutically acceptable acid addition salt of Trunkamide A. The Trunkamide A or salt thereof may be administered in the form of a pharmaceutical composition.

The present invention also relates to pharmaceutical compositions which contain Trunkamide A, or a pharmaceutical acceptable acid addition salt thereof, and a pharmaceutically acceptable carrier, as well as a process for preparation of such compositions.

Examples of pharmaceutical compositions of this invention include any solid (tablets, pills, capsules, granules, etc.) or liquid (solutions, suspensions or emulsions) formulation for oral, topical, parenteral or further mode of administration. They may contain the compound in combination with other pharmacologically active compounds. These compositions may need to be sterile when administered parenterally.

The correct dosage of a pharmaceutical composition comprising Trunkamide A will vary according to the pharmaceutical formulation, the mode of application, and the particular situs, host and bacteria or tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The present invention further provides a method of synthesis of the new compound trunkamide A. Trunkamide A is a cyclic peptide, and conventional techniques for the preparation of such peptides can be adopted without difficulty. For example, trunkamide A can be regarded as a cyclized form of the linear peptide L-Pro-Tzn.L-Phe-L-Dat-L-Das-L-Ile-L-Ala, where Tzn.Phe is phenylalanine thiazoline, Dat is dimethylallylthreonine, and Das is dimethyallylserine. Illustratively such a linear peptide can be prepared and cyclised in accordance with the following reaction scheme:

3 4
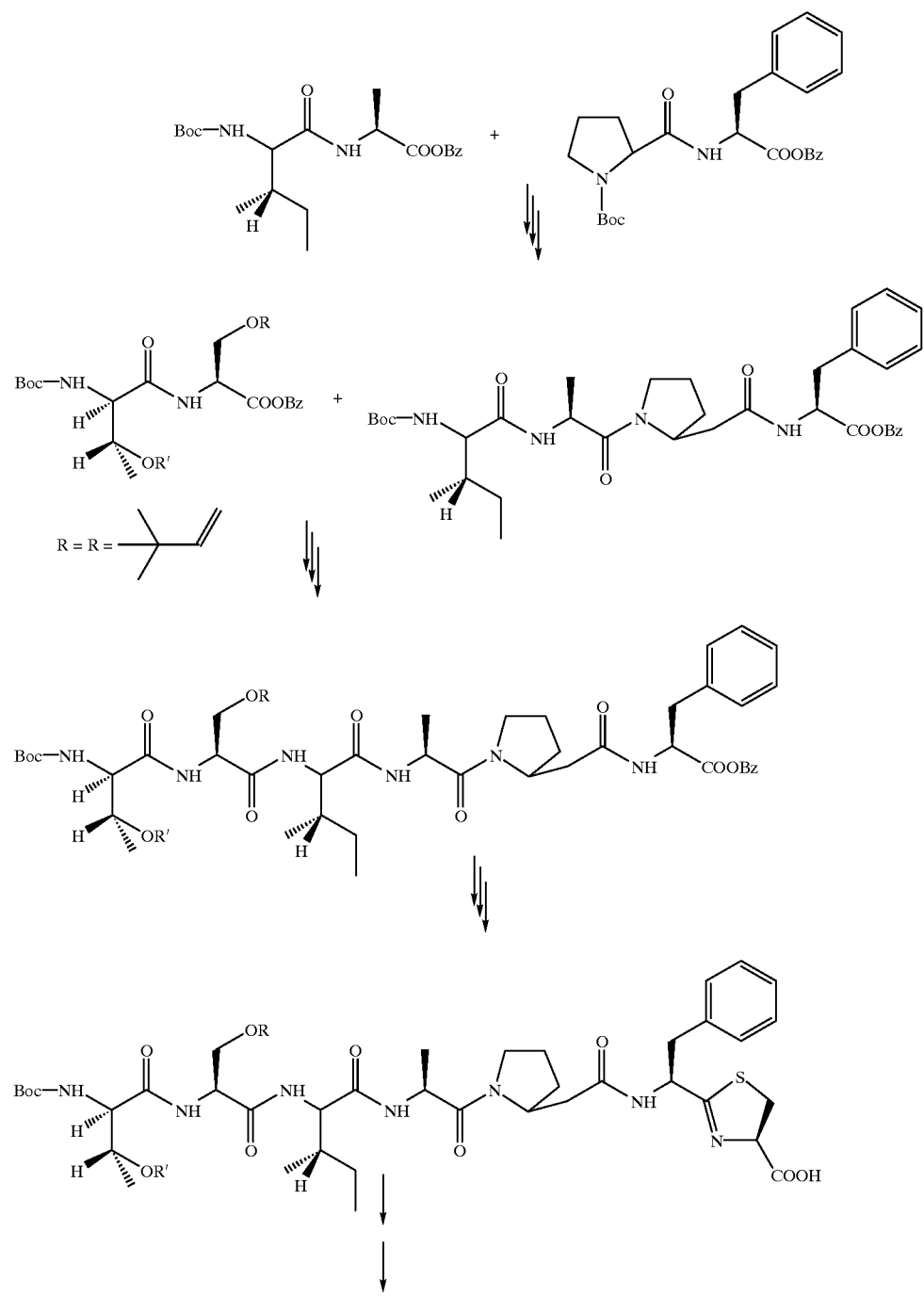
R = R = (prenyl group)

-continued

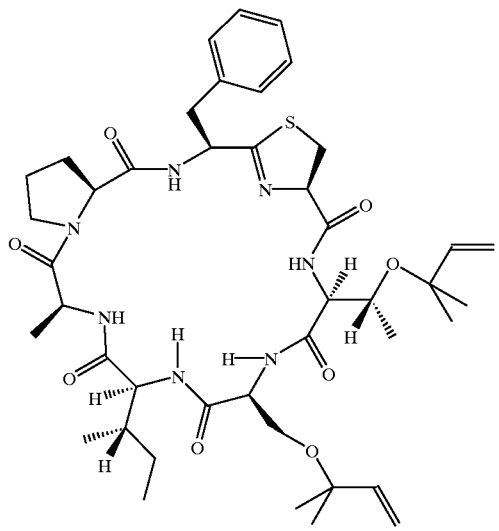

In this sequence, the tetrapeptide unit Phe-Pro-Ala-Ileu is prepared with the carboxyl of the Phe protected as a benzyl ester or other suitable group. The Ser-Thr unit is separately prepared with the hydroxy groups protected with readily removable groups, and then reacted with the tetrapeptide. The resultant hexapeptide will have for instance a benzyl ester on the Phe and a Boc group protecting the amino group of the Thr. The benzyl group can be removed by hydrolysis, and the thiazoline ring constructed from the oxazole , as described in J. Org. Chem. 1996, 61, 6556–6562. Removal of the Boc group then permits cyclisation, to give a cyclic protected peptide. Removal of the hydroxy protecting groups and replacement with mesylate or tosylate allows nucleophilic displacement by 2-methyl-3-buten-2-ol.

Other synthetic procedures can be employed, both by way of minor variation of the above procedure, or by gross variation based on the synthesis of alternative linear peptides for cyclisation.

Trunkamide A is a new cyclic heptapeptide which was isolated from an Australian sample of an ascidian. The small green and white colonial ascidian, Lissoclinum sp., was collected at Bramble and Little Trunk Reefs, Great Barrier Reef, Australia. Co-ordinates for Bramble Reef are 18.25 S, 146.43 E, and co-ordinates for Little Trunk Reef are 18.22 S, 146.50 E. The ascidian is indistinguishable from *Lissoclinum patella*, and colonies are generally 1–3 cm in diameter. The colonies are sporadic on a number of other reefs within the Great Barrier Reef system. A preserved specimen of the Lissoclinum sp. has been deposited at the Museum of Tropical North Queensland, Townsville, North Queensland, Australia. Extraction of the freeze dried tissue from the collected Lissoclinum sp. with dichloromethane followed by purification of the extract on silica gel yielded two fractions. Reversed phase high performance liquid chromatography of the polar fraction yielded trunkamide A and other compounds.

Thus, the present invention also provides a process for the preparation of trunkamide A which comprises extraction from a trunkamide A-producing ascidian Lissoclinum sp.

The Trunkamide A is preferably provided in substantially pure form. In particular, the Trunkamide A is usually substantially free from cellular components or debris of Lissoclinum sp.

EXAMPLES OF THE INVENTION

The present invention will be further illustrated with reference to the following examples which aid in the understanding of the present invention, but which are not limitations thereof. All percentages reported herein, unless otherwise specified, are by weight. All temperatures are expressed in degrees Celsius. All incubations are carried out at 28° C. and flasks are shaken in an orbital shaker at 250 rpm. All media and recipients are sterile and all culture processes aseptic.

SAMPLE COLLECTION AND EXTRACTION

Lissoclinum sp., a small green and white colonial ascidian, was collected at Bramble and Little Trunk Reefs, in the central section of the Great Barrier Reef, Australia in June 1992 using SCUBA (−3 m) and freeze dried before being examined. The freeze dried Ascidians (91 g) were extracted exhaustively first with dichloromethane and then with methanol. The dichloromethane extract was concentrated yielded a dark green residue (0.88 g). This residue was rapidly chromatographed on silica gel (Merck Silica gel, type 60) with a solvent gradient from light petroleum to acetone to methanol. The fraction that eluted with light petroleum/acetone (1:1) was further chromatographed on silica gel with light petroleum/acetone (4:1) to yield lissoclinoide (1.40 mg) and a fraction containing a mixture of a number of peptides. This peptide fraction was purified on reverse phase h.p.l.c. {elution with methanol/water (8.2)} yielding trunkamide A (2.15 mg 0.016%).

Trunkamide A was obtained as a colorless oil $[\alpha]_D$ −231° (c, 0.06 in CHCl$_3$). Found: (h.r.e.i.m.s.) M$^+$, 837.4487. Calc. For C$_{43}$H$_{63}$N$_7$O$_8$S: M$^+$, 837.4459. $\lambda_{max}$(EtOH) 248 nm (14300). $\nu_{Max}$ (CHCl$_3$) 3683, 3619, 3413, 3018, 2976, 1727, 1667, 1664, 1603, 1517, 1476, 1424, 1390, 1222, 1078, 1046, 929, 909, 877, 850 cm$^{-1}$. e.i. mass spectrum m/z 837 (M, 46%), 768 (28), 715 (100), 700 (48), 656 (66), 589 (25), 302 (40), 188 (69), 167 (78), 126 (60).

The N. M. R. spectral data for Trunkamide A in CDCl$_3$ was as follows:

| atom | $\delta^{13}_C$ (no. Attached $^1$H) | $\delta^1_H$ (mult, j(Hz), intgrtn) |
|---|---|---|
| 1 | 171.1 (0) | — |
| 2 | 59.8 (1) | 4.38 (t, 5.4, 1H) |
| 3 | 28.5 (2) | 1.80 (m, 1H) |
|   |           | 1.80 (m, 1H) |
| 4 | 25.5 (2) | 2.30 (m, 1H) |
|   |           | 1.80 (m, 1H) |
| 5 | 47.1 (2) | 3.50 (m, 1H) |
|   |           | 3.52 (m, 1H) |
| 7 | 170.0 (0) | — |
| 8 | 47.7 (1) | 4.49 (dq, 6.1, 6.1, 1H) |
| 9 | 17.8 (3) | 1.20 (d, 6.1, 3H) |
| 10 | — | 7.20 (d, 6.1, 1H) |
| 11 | 170.5 (0) | — |
| 12 | 57.9 (1) | 4.55 (m, 1H) |
| 13 | 36.5 (1) | 2.50 (m, 1H) |
| 14 | 23.6 (2) | 1.35 (m, 1H) |
|    |          | 1.35 (m, 1H) |
| 15 | 11.9 (3) | 0.95 (t, 6.9, 3H) |
| 16 | 16.1 (3) | 0.95 (d, 6.9, 3H) |
| 17 | — | 6.32 (d, 9.6, 1H) |
| 18 | 170.9 (0) | — |
| 19 | 56.5 (1) | 4.55 (ddd, 3.1, 1.6, 8.0, 1H) |
| 20 | 62.2 (2) | 3.44 (dd, 3.1, 9.1, 1H) |
|    |          | 3.89 (dd, 1.6, 9.1, 1H) |
| 22 | 78.0 (0) | — |
| 23 | 25.6 (3) | 1.50 (s, 3H) |
| 24 | 27.3 (3) | 1.35 (s, 3H) |
| 25 | 142.0 (1) | 5.91 (dd, 10.8, 17.6, 1H) |
| 26 | 115.7 (2) | 5.27 (d, 17.6, 1H) |
|    |           | 5.23 (d, 10.7, 1H) |
| 27 | — | 7.55 (d, 8.0, 1H) |
| 28 | 168.6 (0) | — |
| 29 | 55.2 (1) | 4.55 (dd, 5.2, 7.0, 1H) |
| 30 | 67.2 (1) | 4.02 (dq, 5.2, 5.9, 1H) |
| 31 | 18.5 (3) | 1.10 (d, 5.9, 3H) |
| 33 | 77.0 (0) | — |
| 34 | 25.6 (3) | 1.25 (s, 3H) |
| 35 | 25.6 (3) | 1.25 (s, 3H) |
| 36 | 142.6 (1) | 5.73 (dd, 10.9, 17.5, 1H) |
| 37 | 114.9 (2) | 5.15 (d, 10.5, 1H) |
|    |           | 5.11 (d, 17.6, 1H) |
| 38 | — | 7.93 (d, 7.0, 1H) |
| 39 | 170.1 (0) | — |
| 40 | 78.1 (1) | 4.92 (t, 11.5, 1H) |
| 41 | 36.4 (2) | 3.71 (t, 11.3, 1H) |
|    |          | 3.62 (t, 11.3, 1H) |
| 43 | 173.3 (0) | — |
| 45 | 52.6 (1) | 5.25 (ddd, 5.6, 6.1, 8.0, 1H) |
| 46 | 40.0 (2) | 2.90 (dd, 6.1, 13.8, 1H) |
|    |          | 3.20 (dd, 5.6, 13.8, 1H) |
| 47 | 135.6 (0) | — |
| 48 | 129.6 (1) | 7.15 (m, 1H) |
| 49 | 128.3 (1) | 7.25 (m, 1H) |
| 50 | 127.1 (1) | 7.26 (m, 1H) |
| 51 | 128.3 (1) | 7.25 (m, 1H) |
| 52 | 129.6 (1) | 7.15 (m, 1H) |
| 53 | — | 7.30 (d, 8.0, 1H) |

Trunkamide A was shown by h.r.e.i.m.s. to have a molecular formula $C_{43}H_{63}N_7O_8S$. The $^{13}C$ n.m.r. spectrum contained 39 resonances including signals at 129.6 and 128.3 p.p.m. (each from two equivalent aromatic carbon atoms), and a signal for three coincident methyl carbons at 25.6 p.p.m. A combination of DEPT and CH-correlation experiments allowed all of the protonated carbons to be assigned. The presence of seven quaternary carbon signals between 174 and 167 p.p.m. in the $^{13}C$ n.m.r. spectrum and five amide proton doublets in the $^1H$ n.m.r. spectrum suggested a heptapeptide with a Pro and Tzn unit. Analysis of data from multiple n.m.r. experiments and h.p.l.c. of hydrolysis products after Marfey derivatization (Carlsberg Res. Commun., 1984, 49, 591) indicated L-Pro, L-Ile, L-Ala, L-Das, L-Dat and Tzn-L-Phe residues. The carbonyl carbons from each amino acid exception of Ile were assigned unambiguously from HMBC ions observed from the respective β-protons. Because the $^1H$ n.m.r. chemical shifts of the α-proton of the Dat, Das, and Ile were coincident (at 4.55 p.p.m.) interpretation of the correlations to this cluster of signals was ambiguous. Fortunately, the wealth of other correlations to the carbonyl carbon resonances allowed the amino acid sequence Pro-Tzn-Phe-Dat-Das-Ile-Ala to be established. Assumption of an amide bond linking the Ala carbonyl to the Pro nitrogen closed the cycle. Further support for this sequence came from the N.O.e. difference experiments. Strong N.O.e's between the α-proton of the Pro at 4.38 p.p.m. and the Phe NH at 7.30, between the Ile NH at 6.32 and the Das NH at 7.55, and between the Ala α-proton at 4.49 p.p.m. and the Pro δ-protons at 3.50–3.52 indicated the close spatial proximity of each of these pairs of amino acids. Trunkamide A was thus shown to have the given structure.

Stereochemistry of Trunkamide A

In a typical hydrolysis, the peptide (0.4 mg) was heated in 6 N HCl (5 ml) in a sealed glass tube at 103° C. for 22 h. The resulting hydrolysate was freeze dried, dissolved in distilled water (40 μl) and derivatized with FDAA (0.5 mg) in acetone (60 μl) and 1 N sodium bicarbonate (20 μl) at 40° C. for 1 h. Upon completion of reaction the solution was acidified with 2N HCl (10 μl) and stored in the dark until it was analyzed. h.p.l.c. analysis (C18 Activon goldpak column; linear gradient elution, triethylammonium phosphate (50 mM, pH 3.0)/acetonitrile, 90:10-60:40 in 40 min; 2.0 ml/min; UV detection at 340 nm) of the FDAA derivatized hydrolysates established the stereochemistry of the constituent amino acids. Each peak in the chromatographic trace was identified by comparing its retention time with that of the FDAA derivative of the pure amino acid standard and by coinjection.

Biological Activity of Trunkamide A

Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), $10^{-2}$ M sodium bicarbonate and 0.1 g/l penicillin-G+streptomycin sulfate.

A simple screening procedure was carried out to determine and compare the antitumor activity of this compound, using an adapted form of the method described by Bergeron et al. [Biochem. Bioph. Res. Comm. 1984, 121(3), 848–854]. The antitumor cells employed were P-388 (suspension culture of a lymphoid neoplasm from DBA-2 mouse), A-549 (monolayer culture of a human lung carcinoma), HT-29 (monolayer culture of a human colon carcinoma) and MEL-28 (monolayer culture of a human melanoma).

P-388 cells were seeded into 16 mm wells at $1 \times 10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximate IC50 was determined by comparing the growth in wells with drug to the growth in wells control.

A-549, HT-29 and MEL-28 cells were seeded into 16 mm wells at $2 \times 10^4$ cells per well in 1 ml aliquots of MEM 10FCS containing the indicated concentration of drug. A separate set of cultures without drug was seeded as control growth to ensure that cells remained in exponential phase of growth. All determinations were carried in duplicate. After three days of incubation at 37° C., 10% $CO_2$ in a 98% humid atmosphere, the wells were stained with 0.1% Crystal Violet. An approximate IC50 was determined by comparing the growth in wells with drug to the growth in wells control.

| Antitumor Activity Cell Line $IC_{50}$ ($\mu$g/ml) | |
|---|---|
| P-388 | 0.5 |
| A-549 | 0.5 |
| HT-29 | 0.5 |
| MEL-28 | 1.0 |

We claim:
1. The compound trunkamide A of formula:

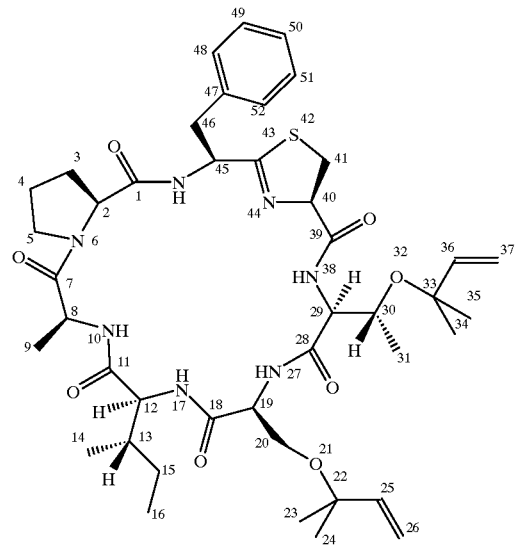

and pharmaceutically acceptable acid addition salts of Trunkamide A.

2. A composition which contains Trunkamide A of formula:

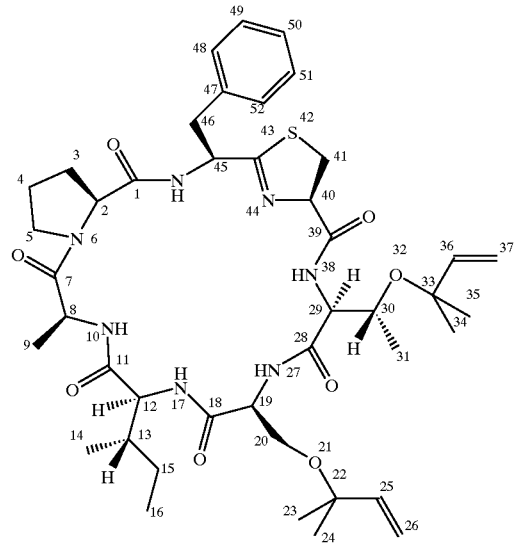

or a pharmaceutically acceptable acid addition salt of Trunkamide A, and a pharmaceutically acceptable carrier.

* * * * *